(12) United States Patent
Nisius et al.

(10) Patent No.: US 6,624,425 B2
(45) Date of Patent: Sep. 23, 2003

(54) WASTE INSPECTION TOMOGRAPHY AND NON-DESTRUCTIVE ASSAY

(75) Inventors: David T. Nisius, Des Plaines, IL (US); George P. Roberson, Tracy, CA (US); David C. Camp, Danville, CA (US); David Entwistle, Buffalo Grove, IL (US)

(73) Assignee: Bio-Imaging Research, Inc., Lincolnshire, IL (US)

(*) Notice: Subject to any disclaimer, the term of this patent is extended or adjusted under 35 U.S.C. 154(b) by 265 days.

(21) Appl. No.: 09/847,929

(22) Filed: May 3, 2001

(65) Prior Publication Data
US 2002/0163988 A1 Nov. 7, 2002

(51) Int. Cl.[7] .............................................. G01T 1/00
(52) U.S. Cl. ................... 250/393; 250/363.01
(58) Field of Search .......................... 250/393, 363.01, 250/391, 376, 357, DIG. 231, 301, 302, 303, 304, 306, 307, 308, 496.1, 493.1; 376/159, 153, 158

(56) References Cited

U.S. PATENT DOCUMENTS 3,597,596 A * 8/1971 Lawless et al. ............. 250/362
4,483,816 A * 11/1984 Caldwell et al. ............ 376/158
4,777,367 A * 10/1988 Kawasaki et al. ........ 250/336.1

FOREIGN PATENT DOCUMENTS

JP         63139284 A  *  6/1988  ............ G01V/5/00

* cited by examiner

Primary Examiner—David Porta
Assistant Examiner—Christine Sung
(74) Attorney, Agent, or Firm—Welsh & Katz, Ltd.

(57) ABSTRACT

A method and apparatus are provided for assaying a waste container. The method includes the steps of forming a plurality of slices through a volume of the waste container, performing a relatively fast passive prescan to measure a level of radioactivity of each of the plurality of slices and identifying at least some slices of the plurality of slices having a relatively high level of radioactivity. In addition, the method includes the steps for performing a relatively fast active prescan of the drum to determine the average attenuation of the plurality of slices. The method further includes the steps of determining an passive assay time for the identified slices based upon the measured radioactivity and average attenuation and performing relatively slow passive and active CT scans of the identified slices based upon the determined passive and active CT assay time to quantify a source of the measured radioactivity by weight.

27 Claims, 3 Drawing Sheets

WASTE INSPECTION TOMOGRAPHY AND NON-DESTRUCTIVE ASSAY

FIELD OF THE INVENTION

The field of the invention relates to nuclear waste and more particularly to methods of measuring the radioactive content of nuclear waste containers.

BACKGROUND OF THE INVENTION

Since the advent of the nuclear age, the presence of nuclear waste has become a significant roadblock to further development of nuclear technology. In the last fifty years, vast amounts of nuclear waste have accumulated.

Nuclear waste is different than other types of waste in that it can kill without direct contact through the effects of radiation. Because of radiation, nuclear waste must be either shielded or stored in protected areas.

While shielding is effective, the added weight creates additional difficulty in storing and moving waste containers. It also adds to the bulk of storage containers.

When nuclear energy first became a factor during World War II (and to a lesser extent even now) nuclear waste was handled in a manner similar to other wastes. In some cases nuclear waste was handled informally with no documentation whatsoever.

What makes nuclear waste more difficult to process than other wastes, however, is the difficulty of identifying and classifying the contents of nuclear waste containers. Every risk associated with chemical and biological waste applies to nuclear waste, with the added factor of the health risks associated with radiation.

In the past, the accepted method for measuring a quantity of a radionuclide within a container has involved the analysis of the entire contents of the container. The analysis of the entire container has been found necessary because of the occasional presence of shielding materials within the container.

Since WWII hundreds of thousands of nuclear waste containers have been filled and stored in a limited number of locations with limited or no regard to what such containers have stored inside them. In order to resolve the problem of nuclear waste, an effort must be made to characterize nuclear waste as a first step in finding a final solution to the disposal of such waste. Accordingly, a need exists for a safe and reliable means of quantitatively measuring the emitted gamma radiations from the nuclear waste within waste containers.

SUMMARY

A method and apparatus are provided for assaying a waste container. The method includes the steps of forming a plurality of slices through a volume of the waste container, performing a relatively fast passive prescan to measure a level of gamma-ray radioactivity of each of the plurality of slices and identifying at least some slices of the plurality of slices having a relatively high level of gamma-ray radioactivity. The method further includes the steps of determining a passive assay time for the identified slices based upon the measured radioactivity. A relatively slow passive scan may then be performed of the identified slices based upon the determined passive assay time to quantify a source of the measured gamma-ray radioactivity by weight.

DETAILED DESCRIPTION OF AN ILLUSTRATED EMBODIMENT

Figure 1:
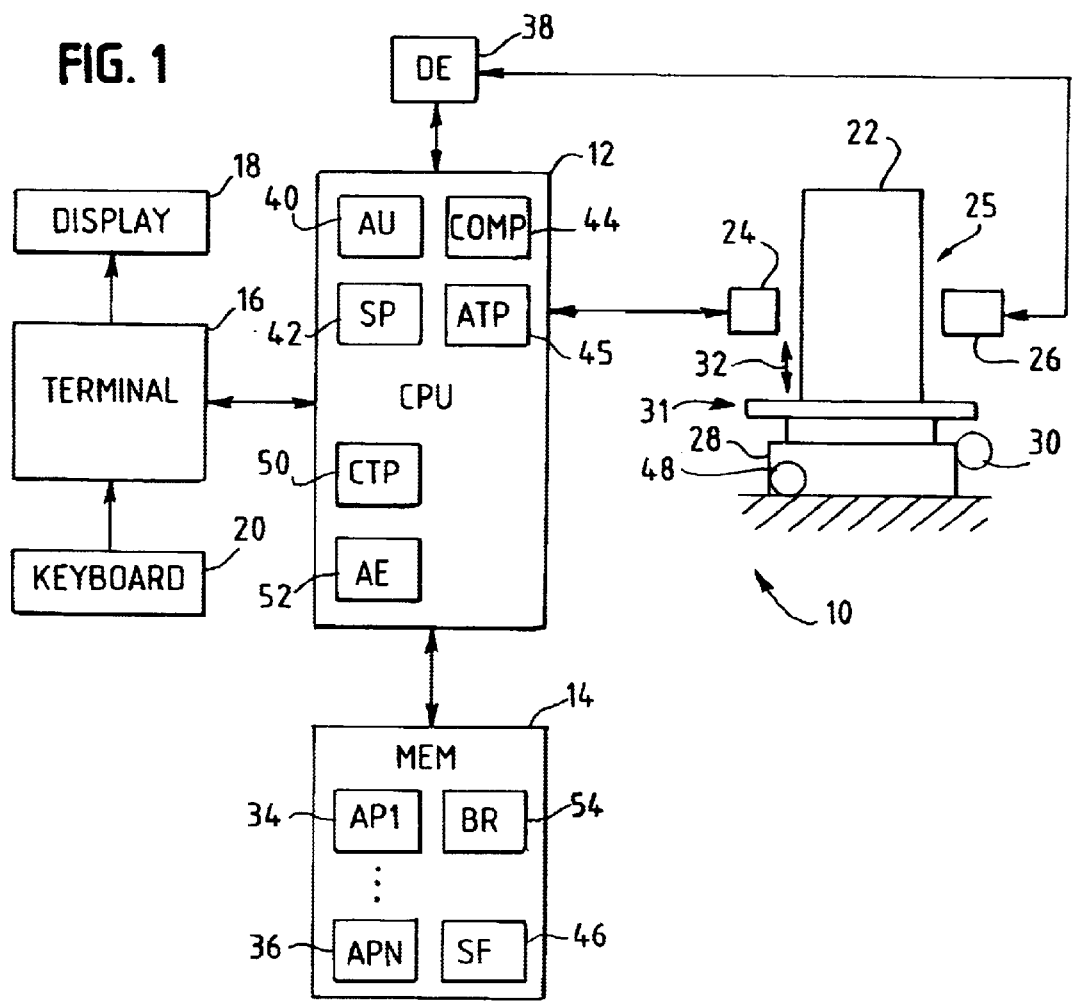
FIG. 1 is a block diagram of a system for assaying a waste container in accordance with an illustrated embodiment of the invention.

FIG. 1 is a block diagram of a non-destructive assaying system 10, shown generally, using waste inspection tomography. Within the system 10, a waste container (e.g., a drum) 22 may be placed upon a barrel manipulator 31 and moved through an interrogation space 25 formed between interrogation devices 24 and 26. Within the interrogation space, one or more of the interrogation devices 24, 26 may interrogate the container 22 under either an active or passive format.

Under an active format, a first interrogation device (e.g., one or more well-collimated radioactive Europium-152 multi-energy gamma-ray radiation sources, each with an approximate source activity of 7 mCi) 24 may function as a source of focused gamma-rays that may pass through and interrogate the container 22 regarding energy-specific attenuation characteristics (effective density). A second interrogation device (e.g., one or more well-collimated high purity germanium (HPGe) detectors) 26 may detect the gamma-rays and form a signal which is related to an effective densit of the container 22 along a line directly connecting the first and second interrogation devices 24, 26.

Under a second, passive format, the first interrogation device 24 may be deactivated (i.e., a shutter 23 may be closed to block any emitted radiation) and the second interrogation device 26 may operate by itself. Under the second format, the second interrogation device 26 may detect gamma-ray radiation from radionuclides located within the container 22 and within the constant solid angle in front of the device 26.

Figure 2:
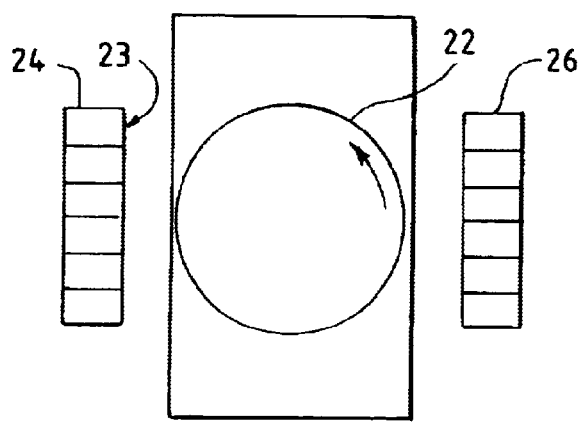
FIG. 2 is a top view of a manipulator that may be used by the system of FIG. 1.

FIG. 2 shows a top view of the container 22 and interrogation devices 24, 26. As shown, the first and second interrogation devices 24, 26 may each be comprised of an array of devices spanning a diameter of the container 22. As shown, the first interrogation device may include six Europium-152 radiation sources 24, each with a blocking shutter 23. The second interrogation device may include six HPGe radiation detectors 26.

The container 22 may be translated through the interrogation space through use of the manipulator 31. An elevator 28 may be used to move 32 the container 22 up or down. A turntable and drive motor 30 may be used to rotate the container 22 within the interrogation space. A shuttle 48 may be used to move the turntable (and container) laterally across the interrogation space 25 to increase the effective sampling provided by the detectors 26.

The manipulators 31 and interrogation devices 24, 26 operate under control of a central processing unit 12 and operators terminal 16. One or more programs 34, 36 may reside within a memory 14 and control the assaying process.

Under control of assay programs 34, 36, the contents of the container 22 may be determined far more accurately than under the prior art. Under illustrated embodiments, the system 10 may use active and passive rapid prescans to identify concentrations of effective density and gama-ray emitting radioactivities. Subsequent, relatively slow active and passive computed tomography (CT) scans may then be used to interrogate only those areas with concentrations of said radioactivities. As used herein, the term "scan" or "prescan" means the movement of the drum 22 with respect to one or more detectors 26 and the measurement of gamma-ray radiation traveling along a predetermined sequence of gamma-ray paths where the measured radiation (and gamma-ray paths) originates from the direction of the contents within the waste container. It should also be noted that a "gamma-ray path" may be referred to, herein, simply as a "ray" when viewed from the perspective of the detector 26 detecting a gamma-ray.

The six sources 24 each typically provide several energies of intense (those with large branching ratios) gamma-rays from 122 keV to 1.4 MeV. This energy range insures that the attenuation characteristics of the contents in a waste drum 22 can be determined at the appropriate energies for a number of transuranic (TRU) radionuclides or other radionuclides.

The six HPGe detectors 26 are characterized by relative efficiencies of greater than 60% at 1.33 MeV. The detector electronics 38 (e.g., model DSPec, provided by EG&G) allows for software control of the peak shaping parameters of gamma-ray energy depositions into the detectors 26. The software control allows the system 10 to employ different detector settings for passive and active data collection, if necessary. Thus, in active mode where the gamma-ray energies are known and the detection rates are high, a slight degradation in energy resolution is acceptable. Thus, the electronics can employ shorter peak-shaping times increasing the live time of the system. (The term "live time" means availability of the detectors and electronics for sampling.) During passive data collection, typical detection rates are not as high and energy resolution plays a more crucial role in the accurate spectroscopic analysis of unknown gamma-rays in the spectrum. Thus, longer shaping times may be utilized while collecting the emission data.

The prescan used by the system 10 may be based upon a technique referred to as a Collimated Gamma Scan (CGS). A passive CGS prescan may be performed first. As a first step, the CPU 12 may send instructions to the manipulator 31 to simultaneously and continuously raise and rotate the container 22. The simultaneous raising and rotation causes the container 22 to spiral through the interrogation space.

As the container 22 spirals through the interrogation space, the six HPGe detectors 26 form a measurement plane that spans the diameter of the drum 22. Gamma-ray spectra from 0 to 2 MeV are collected from each detector 26, summed and recorded to memory (e.g., a disk drive) 14 for each horizontal slice forming the height of the drum 22.

For example, the drum 22 may be a standard 55 gallon drum. The drum may be divided into 16 slices. For each 360 degrees of rotation, the elevator 28 may raise the drum 22 by 2 ¼ inches. The time to sample the 16 slices (raise the elevator 28 to its full height) may be 20 seconds.

The detector electronics 38 of each detector 26 may have a shaping time of 10 microseconds. As a result, as the drum rotates, a sample may be collected from each detector 26 every 10 microseconds. Within a spectrum processor 42, the energy of each sample may be correlated to a particular isotope and a count for that isotope (energy channel) may be incremented. The counts of each energy channel from all the detectors may be summed and stored to disk 14.

Sensitivity to low levels of radioactivity may be increased by the subtraction of a normalzed, site-specific, gamma-ray background spectrum. A background spectrum may be measured by removing the container 22 from the interrogation region 25 and measuring background gamma ray radiation. The measured background gamma-ray radiation may be stored as a background radiation file 54 in memory. During a passive prescan, the background gamma-ray radiation may be retrieved from memory 14 and subtracted from each summed reading within an arithmetic unit 40.

Figure 3:
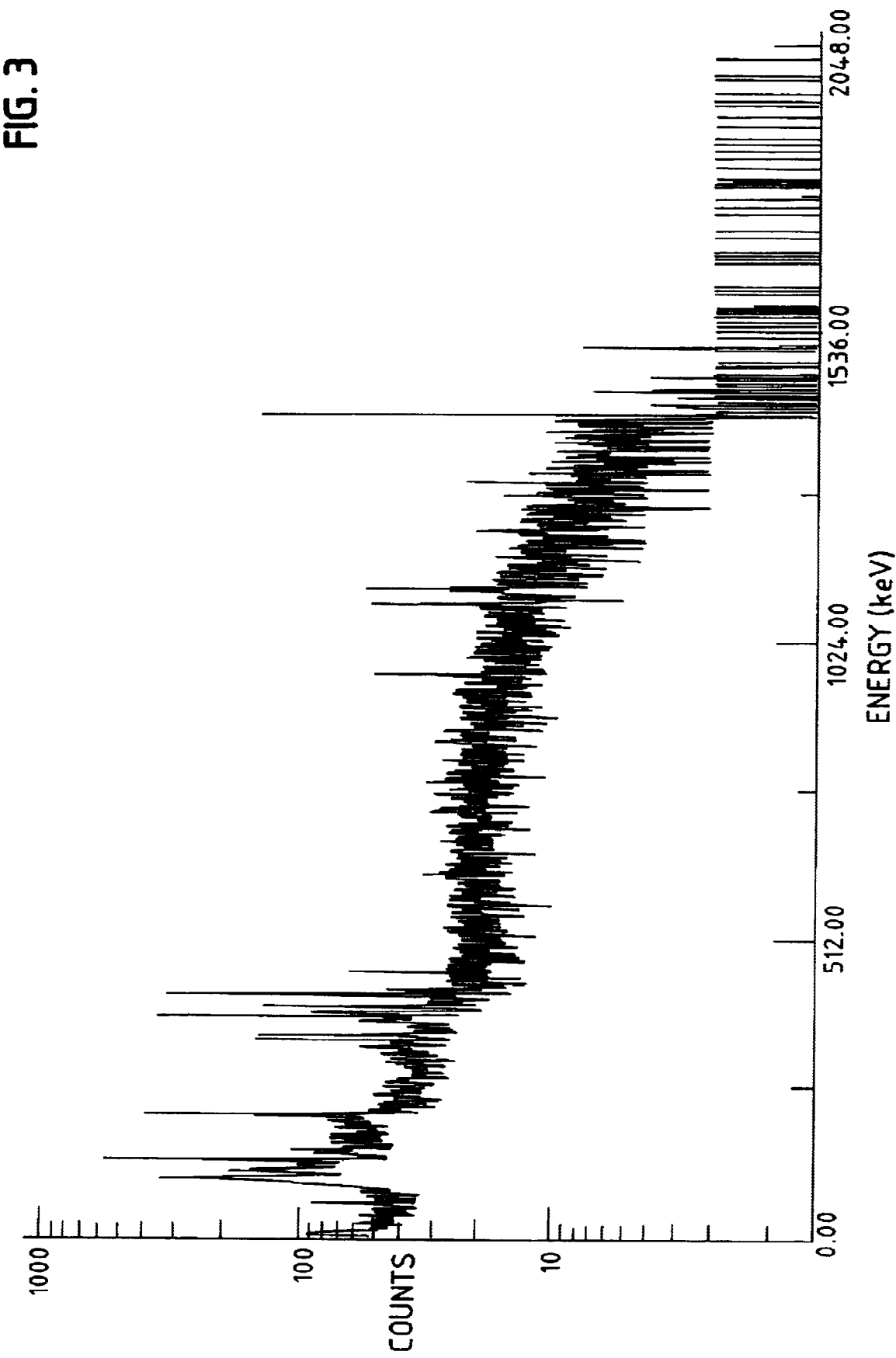
FIG. 3 depicts an energy spectrum that may be measured by the system of FIG. 1 during a passive prescan.

FIG. 3 depicts a slice spectrum that may be measured by the system 10. Distance along the ordinate may be the gamma-ray energy of any gamma-ray emitting radionuclide measured. Distance along the abscissa may be the counts per channel. In the example of FIG. 3, the strong gamma-rays are Pu-239. Also present in FIG. 3 are gamma-rays from Am-241, Pu-241 and Pu-240.

Each background-subtracted, "slice" spectrum is automatically evaluated within a spectrum processor 42 at specific energy regions to determine the existence (i.e., identify the presence) of one or more isotope-specific activity. Evaluation in this context means identifying the gamma-ray energy (i.e., identifying the channel and, thereby, providing one data point for identification of a radionuclide) and measuring the magnitude of that specific energy (i.e., in counts/channel). The energy regions of FIG. 3 that may be monitored can be modified to match the expected radionuclides for given waste streams at different waste generation sites.

Every energy region of interest for each slice spectrum may be evaluated against two gamma-ray peak criteria. First, are the net counts (above a background level) statistically significant? This may be accomplished by requiring that the net counts in a peak be greater than a user-selectable factor (e.g., six times the number of background counts determined for that gamma-ray energy region).

The second criteria has to do with the response characteristics of the HPGe detectors 26. More specifically, is the energy resolution as determined by the full-width-at-half-maximum (FWHM) consistent with what is expected from coaxial HPGe detectors 26 in this energy range? In general, a gamma-ray peak must have a FWHM greater than 1 keV.

In general, determination of whether a slice meets the two described criteria is made in a comparator 44 against one or more threshold values. Slices that meet both criteria are marked for further processing as having significant radionuclides. Marking the slices for further processing may mean placing an identifier of the slice in a slice file 46.

For those vertical slices meeting both peak criteria, an assay time of a particular radionuclide for passive CT may be calculated within a passive assay time processor (ATP) 45 to ensure that a minimum number of counts for every angular view is achieved. The minimum number of counts is an easily adjustable parameter chosen to ensure a statistically accurate reading. Thus, the assay's statistical degree of precision can be set by the user to meet the applicable program requirements (e.g., published nuclear safeguards, TRU waste standards, etc.). The formula for calculating the passive CT assay time per angular view may be characterized as follows:

ASSAY TIME=(MINIMUM COUNTS)/(NET COUNTS)*(CGS TIME),

Where NET COUNTS is the net area under a peak within an energy region of interest (FIG. 3), CGS TIME is the data collection time (e.g., 120 seconds) and MINIMUM COUNTS is the adjustable parameter in the setup discussed above (e.g., 50 counts).

Any number of gamma-ray energy regions may be analyzed simultaneously. This analysis may reveal that different energy regions (corresponding to different radionuclides) have (and require) radically different passive CT assay times. Rules that may be used to determine which assay times will prevail may be described as follows. First, related radionuclides are those that are either related as progeny or those that originated from the same production process. In this case, the rule is simple. The expected "dominant" radionuclide (i.e., the radionuclide providing the greatest counts/channel) is chosen. Alternatively, a user-selectable multiplication factor may be applied to select an expected less dominant radionuclide if its net counts exceed that of the "dominant" radionuclide by the multiplication factor. The end result of this rule, in all cases, is that the radionuclide with the fastest passive CT assay time is chosen.

In other cases, where other radionuclides are present, the assay may proceed with an assay time determined for the radionuclide selected. Where the radionuclide selected is not the dominant radionuclide, the assay will proceed with a slower assay rate chosen to ensure adequate statistics for assaying the significant, but unrelated radionuclide.

After the passive CGS prescan, an active CGS prescan may be performed. The active CGS prescan may be performed by lowering the drum 22 using the same spiral motion used in raising the drum 22.

During the active CGS prescan, the shutters 23 on the six multiple energy, gamma-ray sources may be opened and the sources used to interrogate the attenuating properties of the drum 22 on a slice-by-slice basis. The six HPGe detectors 26 may be used to detect the attenuated signals from the six sources 24.

Figure 4:
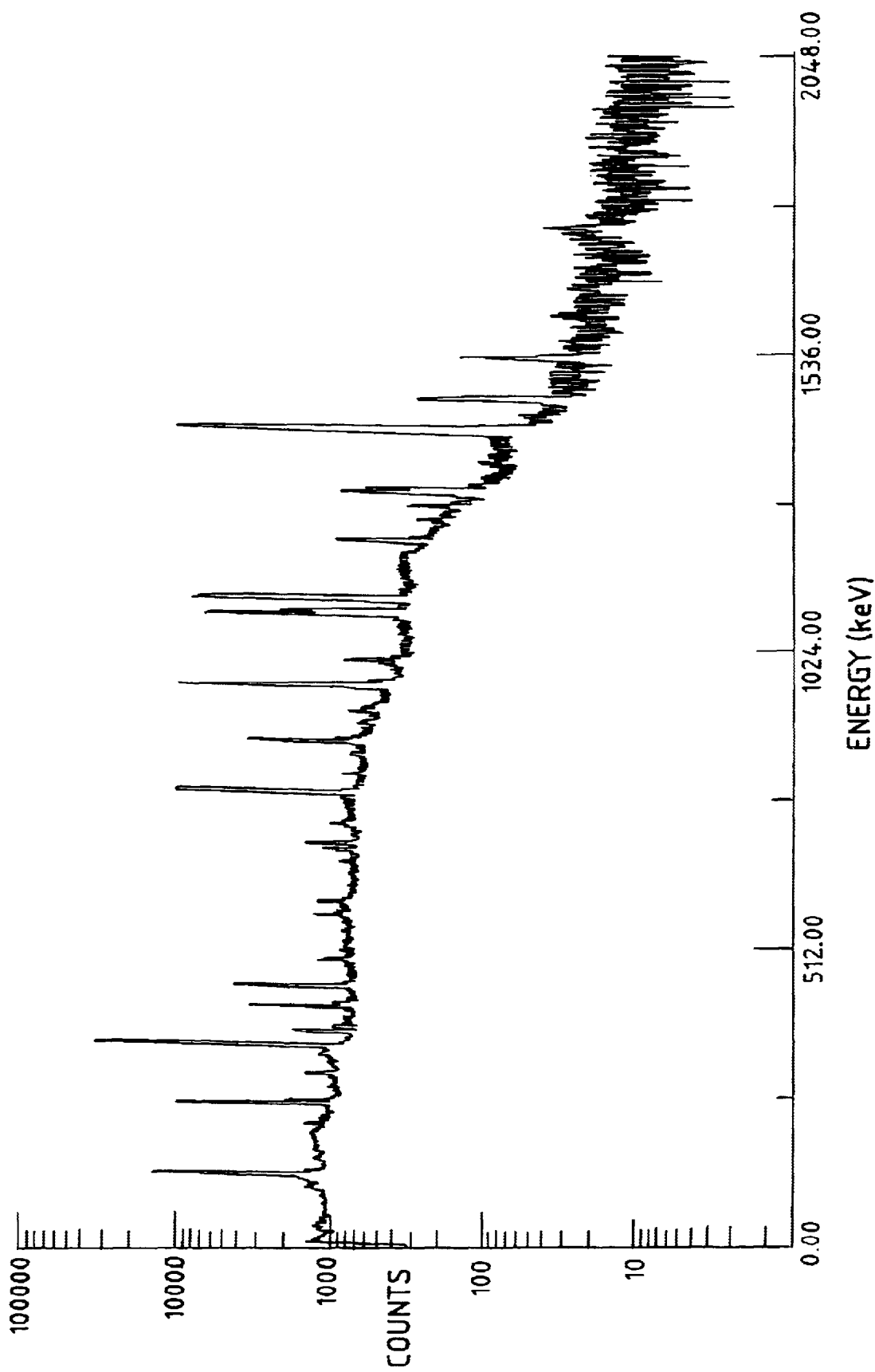
FIG. 4 depicts an energy spectrum that may be measured by the system of FIG. 1 during an active prescan.

The active CGS prescan may use the ame peak detection criteria for gamma-rays within the detector electronics 38 as was used in the passive CGS prescan. One difference, however, is that the gamma-rays of the sources 24 measured within the detectors 26 are well known and limited to a precise region of the slice spectrum (e.g., the Eu-152 gamma-ray peaks shown in FIG. 4). Another difference is that no background subtraction is typically needed.

From the active CGS prescan, an active CT assay scan time is calculated within an active assay time processor 45. The active assay time may use the same equation although the parameters within the equation may be different as in the passive case (shown above).

It should be noted in passing, that the passive CGS prescan determines which slices to assay. From those horizontal slices which will be assayed, the slowest assay time is chosen. The passive CT scan times can be normalized to each other based upon the calculated active scan times. Normalizing the passive CT scan times based upon the active scan times allows the passive CT scan times to be adjusted to a detected effective density of the drum 22.

Once the passive and active assay times have been determined, an active and passive CT scan may be performed on only those slices identified during the passive prescan with gamma-ray peaks above the threshold value. An oversample option allows for an additional 1 or 2 slices to be scanned on either side of the slices with peaks present.

During active and passive CT, the elevator 28 may be activated to raise or lower the drum 22 into a position to process an identified slice. The turntable and rotation motor 30 may then be activated to rotate the drum 22 for collection of information. The one or two additional slices on either side of an identified slice may be used to accommodate differences between the spiral motion of the prescan and the static position of the elevator 28 during CT measurements.

In passive CT, six rays over the entire 0–2 MeV energy range are collected simultaneously from the six detectors 26 within each of nine angular views of the drum 22 for each slice using the predetermined passive scan time. The nine angular views are distributed over a full 360 degree rotation. Each of the nine angular views, therefore, equate to 40 degrees. Further, the drum 22 may rotate continuously during data collection of each view.

For example, if the passive assay time were calculated to be 20 seconds for each view, then the drum 22 would rotate 40 degrees in 20 seconds. At the end of each 20 second period, data from the detector electronics 38 (i.e., the number of counts for each energy channel) would be sent to the CPU 12. The process of measuring and storing data of each view continues until each identified slice has been measured.

At the end of the passive CT scan, an active CT scan would be performed, again on only those slices identified during the prescan. For the same slices, 18 views are collected over 180 degrees of rotation (i.e., 10 degrees per view. The turntable rotates the 10 degrees during each view during the predetermined active assay time.

After the first 18 views are collected, the shuttle 48 may be activated to provide a lateral translation (allowing the drum to be measured in a second position). The lateral translation may be equal to one half the distance between detectors 26. Within the second position another 18 views may be collected. The lateral translation allows the six detectors 26 to collect information along 12 rays passing through the drum 22.

During the active CT, only the total counts, background counts and net counts for gamma-rays originating from the active source 24 and detected by the detectors 26 may be stored to file. During passive CT, each ray sum (of each view) may be passed to the spectrum processor 42 where several unique functions may be performed. First, a normalized detector-specific background spectrum may be subtracted from each passive ray spectrum. This normalization is not done by counting time, but by the peak areas of the background gamma-rays in the two spectra. This subtraction reduces the Compton-background contribution from gamma-rays that did not originate from the drum 22 and, thus, it increases the peak sensitivity for gamma-rays which were, in fact, emitted from within the drum 22. It should also be noted that this technique could also be used to subtract higher-energy gamma-rays emitted from within the drum 22 to, thereby, increase assay sensitivity for gamma-rays that lie at lower energies.

The spectrum processor 42 also performs other functions. For example, a routine within the spectrum processor 42 may extract peak and any background counts for each energy region that may be assayed and may do this for every ray (detector 26). Information gathered through this process provides the information necessary to perform CT reconstruction for the emission range. Because all data is stored to disk 14, additional energy regions of interest may be analyzed at a later date for further information.

Finally, a routine of the spectrum processor 42 sums every passive ray to form an inclusive statistics spectrum for all the slices that were assayed. From this spectrum, isotopic ratios may be determined automatically by fitting gamma-ray peaks corresponding to different isotopes. These ratios may be determined in limited energy regions so that efficiency and attenuation differences are minimal. Also, a gamma-ray energy library may be used to identify unknown peaks in the spectrum.

After the spectroscopy routine, the transmission CT image may be reconstructed for the slices that were assayed. The emission and transmission data may then be provided as an input to an optimization routine within a CT processor 50 based on a constrained conjugate gradient search that determines the attenuation-corrected radioactivity inside the drum 22. By knowing the radiation originating from each voxel (volume element), the total quantity of the radionuclide present within the container 22 may be determined. The total weight may be determined by summing within an assaying processor 52 the weight of the radionuclide present within each voxel.

From the isotopic ratios, the activity (and quantity) of all related isotopes can also be determined. Then, depending on the goals of the program, a set of isotope-specific constants can be applied to the activity levels to convert to quantities such as total radioactivity, fissile gram equivalent, TRU alpha-activity, alpha-activity, pulmonary equivalent activity, decay heat and mass.

In order to provide an accurate absolute assay of the radionuclides within the drum 22, the measured radiation emanating from the drum 22 must be corrected for the matrix attenuation it experiences. This correction requires knowledge of the spatial distribution of both emitters and the effective density of absorbers.

To provide an accurate absolute assay, the active CT data is acquired and reconstructed using a robust 2-D filtered backprojection algorithm (e.g., Image Reconstruction from Projections Implementation and Applications, G. T. Herman, Ed. (Springer Verlag, N.Y., 1979)). The resultant 2-D active CT slice data at a particular energy may be merged into a 3-D array of linear attenuation values before it is submitted with the passive count data to the passive CT image reconstruction and assay algorithm operating within the CT processor 50. Any of a number of passive reconstruction algorithms may be used (e.g., J. A. Jackson, D. Goodman, G. P. Roberson, H. E. Martz, "An Active and Passive Computed Tomography Algorithm with a Constrained Conjugate Gradient Solution", Proceedings of the 6th Nondestructive Assay and Nondestructive Examination Waste Characterization Conference, Salt Lake City, Utah, Nov. 17–19, 1998).

In order to assay the 3-D structure of the drum 22, it may be divided into a set of voxels (i.e., volume elements). The number of counts for each detectable radionuclide is determined for each voxel. The passive CT image reconstruction and assay may begin by defining a vector p, where the elements in the vector are the number of counts from each voxel. The vector p is unknown and is the desired solution. The emitted radiation of the passive scan is measured at a series of detector positions, which constitute the ray sums in the passive CT scan. The vector $g\gamma$ is defined, where each element in the vector is the measured radiation at a given detector position. The vector $g\gamma$ is the sinogram data measured in the passive CT scan. The relationship between the vectors p and $g\gamma$ can be defined mathematically by the expression $g\gamma = Ap$.

The system matrix A represents and incorporates the effects of the system's geometry and the attenuation image determined from the active CT scan. The matrix A may be too large to be effectively inverted to solve for p. Therefore, p may be determined from $g\gamma$ and A using an iterative optimization technique.

The iterative active and passive CT reconstruction codes operating within the CT processor 50 may be conventional and may be divided into an optimization and a model code. The optimizer may consist of a cost function and a minimizer algorithm. The cost function calculates a scalar by comparison of the measured quantity $g\gamma$ with the calculated quantity $\hat{g}\gamma$, which is a passive sinogram. The minimizer may be used to search for a next best solution, $\hat{p}$. The model code may determine the calculated passive sinogram from the current solution determined by the minimizer. The optimizer may determine when the solution is acceptable, producing a final $\hat{p}$.

A specific embodiment of a method and apparatus for assaying a waste container has been described for the purpose of illustrating the manner in which the invention is made and used. It should be understood that the implementation of other variations and modifications of the invention and its various aspects will be apparent to one skilled in the art, and that the invention is not limited by the specific embodiments described. Therefore, it is contemplated to cover the present invention any and all modifications, variations, or equivalents that fall within the true spirit and scope of the basic underlying principles disclosed and claimed herein.

What is claimed is:

1. A method of assaying a waste container comprising the steps of:

forming a plurality of slices through a volume of the waste container;

performing a relatively fast passive prescan to measure a level of gamma-ray radioactivity of each of the plurality of slices;

identifying at least some slices of the plurality of slices having a relatively high level of gamma-ray radioactivity;

determining a passive assay time for the identified slices based upon the measured radioactivity; and performing a relatively slow passive scan of the identified slices based upon the determined passive assay time to quantify a source of the measured radioactivity by weight.

2. The method of assaying a waste container as in claim 1 wherein the step of performing the relatively fast passive prescan and relatively slow passive scan further comprises measuring a radioactivity and energy specific attenuation coefficient along a plurality of paths through each of the plurality of slices.

3. The method of assaying a waste container as in claim 2 wherein the step of identifying slices having a relatively high level of radioactivity further comprises comparing the measured radioactivity with a predetermined threshold value.

4. The method of assaying a waste container as in claim 2 wherein the step of performing the relatively slow radioactivity scan to quantifying the source of the measured gamma-ray radiation further comprises determining a quantity of a gamma-ray emitting radionuclide providing the measured radioactivity in each voxel of the identified slices using computed tomography.

5. The method of assaying a waste container as in claim 4 wherein the step of quantifying the source of the measured radioactivity further comprises summing the determined quantity of the radionuclide in each voxel of the identified slices.

6. The method of assaying a waste container as in claim 1 further comprising performing a relatively fast active prescan of the plurality of slices using a pre-selected radioactive source.

7. The method of assaying a waste container as in claim 6 further comprising determining an active assay time for the identified slices based upon the measured energy-specific attenuation coefficients of the identified at least some slices.

8. The method of assaying a waste container as in claim 7 further comprising performing a relatively slow active scan of the identified slices based upon the determined assay time to quantify energy-specific attenuation coefficients of the identified slices.

9. The method of assaying a waste container as in claim 8 wherein the step of performing the relatively slow active scan to quantify the energy-specific attenuation coefficients of the identified slices further comprises determining energy-specific attenuation coefficients of each voxel of the identified slices using computed tomography.

10. The method of assaying a waste container as in claim 9 further comprising adjusting the measured radiation along each of the plurality of paths based upon a determined energy-specific attenuation coefficient of each voxel along the path.

11. An apparatus for assaying a waste container comprising:
    means for forming a plurality of slices through a volume of the waste container;
    means for performing a relatively fast passive prescan to measure a level of gamma-ray radioactivity within each of the plurality of slices;
    means for identifying at least some slices of the plurality of slices having a relatively high level of radioactivity;
    means for determining a CT passive assay time for the identified slices based upon the measured radioactivity; and
    means for performing a relatively slow CT passive scan of the identified slices based upon the determined passive assay time to quantify a source of the measured gamma-ray radioactivity by weight.

12. The apparatus for assaying a waste container as in claim 11 wherein the means for performing the relatively fast passive prescans and relatively slow passive scan further comprises means for measuring a radioactivity and an energy-specific attenuation coefficient along a plurality of paths through each of the plurality of slices.

13. The apparatus for assaying a waste container as in claim 12 wherein the means for identifying slices having a relatively high level of radioactivity further comprises means for comparing the measured radioactivity with a predetermined threshold value.

14. The apparatus for assaying a waste container as in claim 12 wherein the means for performing the relatively slow radioactivity scan to quantifying the source of the measured radiation further comprises means for determining a quantity of a gamma-ray emitting radionuclide providing the measured radioactivity in each voxel of the identified slices using computed tomography.

15. The apparatus for assaying a waste container as in claim 14 wherein the means for quantifying the source of the measured radioactivity further comprises means for summing the determined quantity of the radionuclide in each voxel of the identified slices.

16. The apparatus for assaying a waste container as in claim 11 further comprising means for performing a relatively fast active prescan of the plurality of slices using a predetermined radioactive source.

17. The apparatus for assaying a waste container as in claim 16 further comprising means for determining an active CT assay time for the identified slices based upon the measured energy-specific attenuation coefficients of the identified slices.

18. The apparatus for assaying a waste container as in claim 17 further comprising means for performing a relatively slow active CT scan of the identified slices based upon the determined energy-specific attenuation coefficients assay time to quantify energy-specific attenuation coefficients of the identified slices.

19. The apparatus for assaying a waste container as in claim 18 wherein the means for performing the relatively slow active scan to quantify the energy-specific attenuation coefficients of the identified slices further comprises means for determining energy-specific attenuation coefficients of each voxel of the identified slices using computed tomography.

20. The apparatus for assaying a waste container as in claim 19 further comprising means for adjusting the measured radiation along each of the plurality of paths based upon determined energy-specific attenuation coefficients of each voxel along the path.

21. An apparatus for assaying a waste container comprising:
    a radiation detector adapted to form a plurality of slices through a volume of the waste container;
    a first assay program adapted to perform a relatively fast passive prescan to measure a level of gamma-ray radioactivity of each of the plurality of slices;
    a spectrum processor adapted to identify at least some slices of the plurality of slices having a relatively high level of radioactivity;
    a passive assay time processor adapted to determine an passive assay time for the identified slices based upon the measured radioactivity; and
    a second assay program adapted to perform a relatively slow passive CT scan of the identified slices based upon the determined passive assay time to quantify a source of the measured radioactivity by weight.

22. The apparatus for assaying a waste container as in claim 21 wherein the radiation detector further comprises a set of radiation detectors adapted to measure a radioactivity and energy-specific attenuation coefficient along a plurality of paths through each of the plurality of slices.

23. The apparatus for assaying a waste container as in claim 22 wherein the spectrum processor further comprises a comparator adapted to compare the measured radioactivity with a predetermined threshold value.

24. The apparatus for assaying a waste container as in claim 22 wherein the first and second assay programs further comprises a computed tomography processor adapted to determine a quantity of a radionuclide providing the measured radioactivity in each voxel of the identified slices using computed tomography.

25. The apparatus for assaying a waste container as in claim 24 wherein the computed tomography processor further comprises an assay processor adapted to sum the determined quantity of the radionuclide in each voxel of the identified slices.

26. The apparatus for assaying a waste container as in claim 21 further comprising a radiation source adapted to perform a relatively fast active prescan of the plurality of slices using a predetermined radioactive source.

27. The apparatus for assaying a waste container as in claim 26 further comprising an active assay time processor adapted to determine an active assay time for the identified slices based upon the measured energy-specific attenuation coefficients of the identified slices.

* * * * *